[19] United States Patent
Wertz et al.

[11] Patent Number: 5,716,821
[45] Date of Patent: Feb. 10, 1998

[54] PREVENTION AND TREATMENT OF RESPIRATORY TRACT DISEASE

[75] Inventors: Gail W. Wertz; Qingzhong Yu, both of Birmingham, Ala.

[73] Assignee: UAB Research Foundation, Birmingham, Ala.

[21] Appl. No.: 316,438

[22] Filed: Sep. 30, 1994

[51] Int. Cl.$^6$ ..................................................... C12N 7/00
[52] U.S. Cl. .................................. 435/235.1; 435/320.1; 514/44; 424/93.21
[58] Field of Search ............................ 424/93.21, 93.1; 435/320.1, 240.2, 235.1; 514/44

[56] References Cited

U.S. PATENT DOCUMENTS

| | | | |
|---|---|---|---|
| 4,122,167 | 10/1978 | Buynak et al. | 424/89 |
| 4,145,252 | 3/1979 | Buynak et al. | 195/1.3 |
| 5,149,650 | 9/1992 | Wertz et al. | 435/243 |
| 5,166,057 | 11/1992 | Palese et al. | 435/69.1 |
| 5,194,595 | 3/1993 | Wathen | 530/395 |
| 5,223,254 | 6/1993 | Paradiso et al. | 424/89 |
| 5,288,630 | 2/1994 | Wathen | 435/240.2 |

FOREIGN PATENT DOCUMENTS

| | | |
|---|---|---|
| WO 92/01471 | 7/1991 | WIPO. |
| WO 92/04375 | 7/1991 | WIPO. |
| WO 92/07940 | 11/1991 | WIPO. |
| WO 93/21310 | 4/1993 | WIPO. |

OTHER PUBLICATIONS

Huang et al., "Characterization of the 10 proteins of human respiratory syncytial virus: Identification of a fourth envelope–associated protein", *Virus Research*, 2 (1985) pp. 157–173.

Collins et al., "cDNA Cloning and Transcriptional Mapping of Nine Polyadenylylated RNAs Encoded by the Genome of Human Respiratory Syncytial Virus", *Proc. Natl. Acad. Sci. USA* (Jun. 1983), vol. 80, pp. 3208–3212.

Dickens et al, "Transcriptional Mapping of Human Respiratory Syncytial Virus", *Journal of Virology* (Nov. 1984), vol. 52, No. 2, pp. 364–369.

Collins et al., "Identification of a Tenth mRNA of Respiratory Syncytial Virus and Assignment of Polypeptides to the 10 Viral Genes", *Journal of Virology* (Feb. 1984), vol. 49, No. 2, pp. 572–578.

Satake et al.,"Nucleotide Sequence of the Gene Encoding Respiratory Syncytial Virus Genomic RNA Matrix Protein", *Journal of Virology* (Apr. 1984), vol. 50, No. 1, pp. 92–99.

Satake et al., "Sequence Analysis of the Respiratory Syncytial Virus Phosphoprotein Gene", *Journal of Virology* (Dec. 1984), vol. 52, No. 3, pp. 991–994.

Collins et al., "Nucleotide Sequence of the Gene Encoding the Fusion (F) Glycoprotein of Human Respiratory Syncytial Virus", *Proc. Natl. Acad. Sci. USA* (Dec. 1984), vol. 81, pp. 7683–7687.

Collins et al., "Correct Sequence for the Major Nucleocapsid Protein mRNA of Respiratory Syncytial Virus", *Virology* (1985), vol. 146, pp. 66–77.

Collins et al., "The 1A Protein Gene of Human Respiratory Syncytial Virus: Nucleotide Sequence of the mRNA and a Related Polycistronic Transcript", *Virology* (1985), vol. 141, pp. 283–291.

Collins et al., "Nucleotide Sequences of the 1B and 1C Nonstructural Protein mRNAs of Human Respiratory Syncytial Virus", *Virology*,(1985) vol. 143, pp. 442–451.

Collins et al., "The Envelope–Associated 22K Protein of Human Respiratory Syncytial Virus: Nucleotide Sequence of the mRNA and a Related Polytranscript", *Journal of Virology* (Apr. 1985), vol. 54, No. 1, pp. 65–71.

Wertz et al., "Nucleotide Sequence of the G Protein Gene of Human Respiratory Syncytial Virus Reveals an Unusual Type of Viral Membrane Protein", *Proc. Natl. Acad. Sci. USA* (Jun. 1985), vol. 82, pp. 4075–4079.

Stott et al., "Human Respiratory Syncytial Virus Glycoprotein G Expressed from a Recombinant Vaccinia Virus Vector Protects Mice against Live–Virus Challenge", *Journal of Virology* (Nov. 1986), vol. 60, No. 2, pp. 607–613.

Bangham et al., "Human and Murine Cytotoxic T Cells Specific to Respiratory Syncytial Virus Recognize the Viral Nucleoprotein (N), but not the Major Glycoprotein (G), Expressed by Vaccinia Virus Recombinants", *The Journal of Immunology* (Dec. 1986), vol. 137, No. 12, pp. 3973–3977.

Pemberton et al, "Cytotoxic T Cell Specificty for Respiratory Syncytial Virus Proteins: Fusion Protein is an Important Target Antigen", *J. Gen. Virol.*, (1987) vol. 68, pp. 2177–2182.

Wertz et al., "Expression of the Fusion Protein of Human Respiratory Syncytial Virus from Recombinant Vaccinia Virus Vectors and Protection of Vaccinated Mice", *Journal of Virology* (Feb. 1987), vol. 61, No. 2, pp. 293–301.

King et al. "Recombinant Vaccinia Viruses Carrying the N Gene of Human Respiratory Syncytial Virus: Studies of Gene Expression in Cell Culture and Immune Response in Mice", *Journal of Virology* (Sep. 1987), vol. 61, No. 9, pp. 2885–2890.

Stott et al., "Immune and Histopathological Responses in Animals Vaccinated with Recombinant Vaccinia Viruses that Express Individual Genes of Human Respiratory Syncytial Virus", *Journal of Virology*, (Dec. 1987), vol. 61, No. 12, pp. 3855–3861.

(List continued on next page.)

Primary Examiner—Jasemine C. Chambers
Assistant Examiner—Deborah Jean Reynolds Clark
Attorney, Agent, or Firm—Benjamin Aaron Adler

[57] ABSTRACT

Recombinant methods for recovering wildtype or engineered negative stranded, non-segmented RNA virus genomes containing non-coding 3' and 5' regions (e.g. leader or trailer regions) surrounding one, several or all of the genes of the virus or one or more heterologous gene(s) in the form of ribonucleocapsids containing N, P and L proteins, which are capable of replicating and assembling with the remaining structural proteins to bud and form virions, or which are only capable of infecting one cell, or are defective interfering particles, are disclosed. Novel vaccines, gene therapy vectors and antiviral compounds are also disclosed.

12 Claims, 4 Drawing Sheets

OTHER PUBLICATIONS

Openshaw et al., "Helper T Cell Recognition of Respiratory Syncytial Virus in Mice", *J. Gen. Virol.* (1988), vol. 69, pp. 305, 312.

Lerch et al., "Characterization of Bovine Respiratory Syncytial Virus Proteins and mRNAs and Generation of cDNA Clones to the Viral mRNAs", *Journal of Virology*, (Feb. 1989), vol. 63, No. 2, pp. 833–840.

Pattnaik et al., "Replication and Amplification of Defective Interfering Particle RNAs of Vesicular Stomatitis Virus in Cells Expressing Viral Proteins from Vectors Containing Cloned cDNAs", *Journal of Virology* (Jun. 1990), vol. 64, No. 6, pp. 2948–2957.

Lerch et al., "Nucleotide Sequence Analysis and Expression from Recombinant Vectors Demonstrate that the Attachment Protein G of Bovine Respiratory Syncytial Virus is Distinct from that of Human Respiratory Syncytial Virus", *Journal of Virology*, (Nov. 1990), vol. 64, No. 11, pp. 5559–5569.

Sullender et al., "The Respiratory Syncytial Virus Subgroup B Attachment Glycoprotein: Analysis of Sequence, Expression from a Recombinant Vector, and Evaluation as an Immunogen against Homologous and Heterologous Subgroup Virus Challenge", *Virology*, (1990), vol. 178, pp. 195–203.

Pattnaik et al, "Cells that Express all Five Proteins of Vesicular Stomatitis Virus from Cloned cDNAs Support Replication, Assembly and Budding of Defective Interfering Particles", *Proc. Natl. Acad. Sci. USA*, (Feb. 1991), vol. 88, pp. 1379–1383.

Sullender et al., "Genetic Diversity of the Attachment Protein of Subgroup B Respiratory Syncytial Viruses", *Journal of Virology*, (Oct. 1991), vol. 65, No. 10, pp. 5425–5434.

Stec et al, "Sequence Analysis of the Polymerase L Gene of Human Respiratory Syncytial Virus and Predicted Phylogency of Nonsegmented Negative–Strand Viruses", *Virology*, (1991), vol. 183, pp. 273–287.

Lerch et al., "Nucleotide Sequence Analysis of the Bovine Respiratory Syncytial Virus Fusion Protein mRNA and Expression from a Recombinant Vaccinia Virus", *Virology*, (1991), vol. 181, pp. 118–131.

Mink et al, "Nucleotide Sequences of the 3' Leader and 5' Trailer Regions of Human Respiratory Syncytial Virus Genomic RNA", *Virology* (1991), vol. 185, pp. 615–624.

Collins et al., "Rescue of Synthetic Analogs of Respiratory Syncytial Virus Genomic RNA and Effect of Truncations and Mutations on the Expression of a Foreign Reporter Gene", *Proc. Natl. Acad. Sci. USA*, (Nov. 1991), vol. 88, pp. 9663–9667.

Amann et al., "Bovine Respiratory Syncytial Virus Nucleocapsid Protein: mRNA Sequence Analysis and Expression from Recombinant Vaccinia Virus Vectors", *Journal of General Virology* (1992), vol. 73, pp. 999–1003.

Cherrie et al, "Human Cytotoxic T Cells Stimulated by Antigen on Dendritic Cells Recognize the N, SH, F, M, 22K, and 1b proteins of Respiratory Syncytial Virus", *Journal of Virology* (Apr. 1992), vol. 66, No. 4, pp. 2102–2110.

Pattnaik et al., "Infectious Defective Interfering Particles of VSV from Transcripts of a cDNA Clone", *Cell*, (Jun. 12, 1992), vol. 69, pp. 1011–1020.

Collins et al., "Rescue of a 7502–Nucleotide (49.3% of Full–Length) Synthetic Analog of Respiratory Virus Syncytial Genomic RNA", *Virology* (1993), vol. 195, pp. 252–256.

Garcia–Sastre, A. and Palese, P., "Genetic Manipulation of Negative–Strand RNA Virus Genomes," *Annu. Rev. Microbiol.*, vol. 47, 765–790 (1993).

Palese, P., "Genetic Engineering of Infectious Negative–Strand RNA Viruses," *Trends in Microbiology*, vol. 3, No. 4, 123–125 (1995).

Pattnaik, A., et al., "The Termini of VSV DI Particle RNAs are Sufficient to Signal RNA Encapsidation, Replication, and Budding to Generate Infectious Particles," *Virology*, vol. 206, 760–764 (1995).

Rice, C., "Examples of Expression Systems Based on Animal RNA Viruses: Alphaviruses and Influenza Virus," *Current Opinion in Biotechnology*, vol. 3, 523–532 (1992).

Wertz, G.W. and Melero, J.A., "Workshop on 'Reverse Genetics of Negative Stranded RNA Viruses' Sponsored by the Juan March Institute, Madrid, Spain," *Virus Research*, vol. 30, 215–219 (1993).

Whelan, S., et al., "Efficient Recovery of Infectious Vesicular Stomatitis Virus Entirely from cDNA Clones," *Proc. Natl. Acad. Sci. USA*, vol. 92, 8388–8392 (1995).

Yamanaka, K., et al., "In Vivo Analysis of the Promoter Structure of the Influenza Virus RNA Genome Using a Transfection System with an Engineered RNA," *Proc. Natl. Acad. Sci. USA*, vol. 88, 5369–5373 (1991).

Yu, Q., et al., "Functional cDNA Clones of the Human Respiratory Syncytial (RS) Virus N, P, and L Proteins Support Replication of RS Virus Genomic RNA Analogs and Define Minimal trans–Acting Requirements for RNA Replication," *Journal of Virology*, 2412–2419 (1995).

International Search Report for PCT/US95/12507, issued Dec. 27, 1995.

Holland, The Viruses: Defective Interfering Rhabdoviruses, 297–360, 1987.

Fuerst et al, Proc. Natl. Acad. Sci. USA, 83:8122–8126, Nov. 1986.

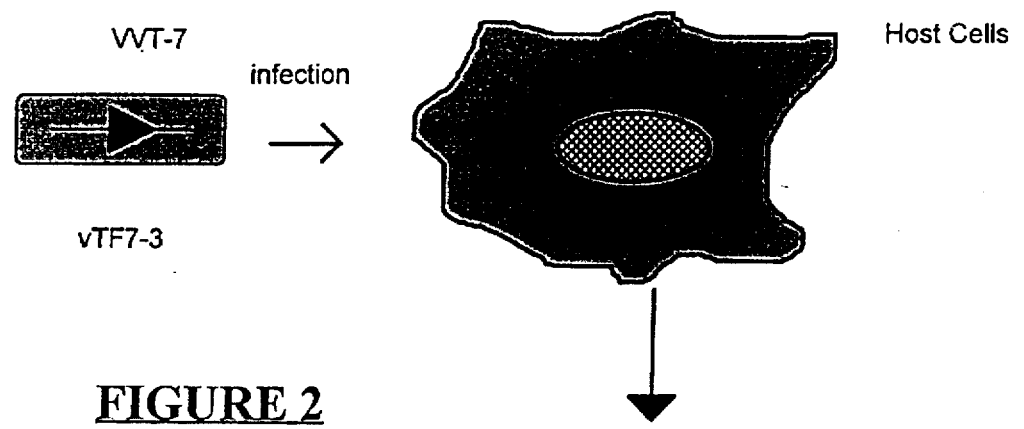
FIGURE 2
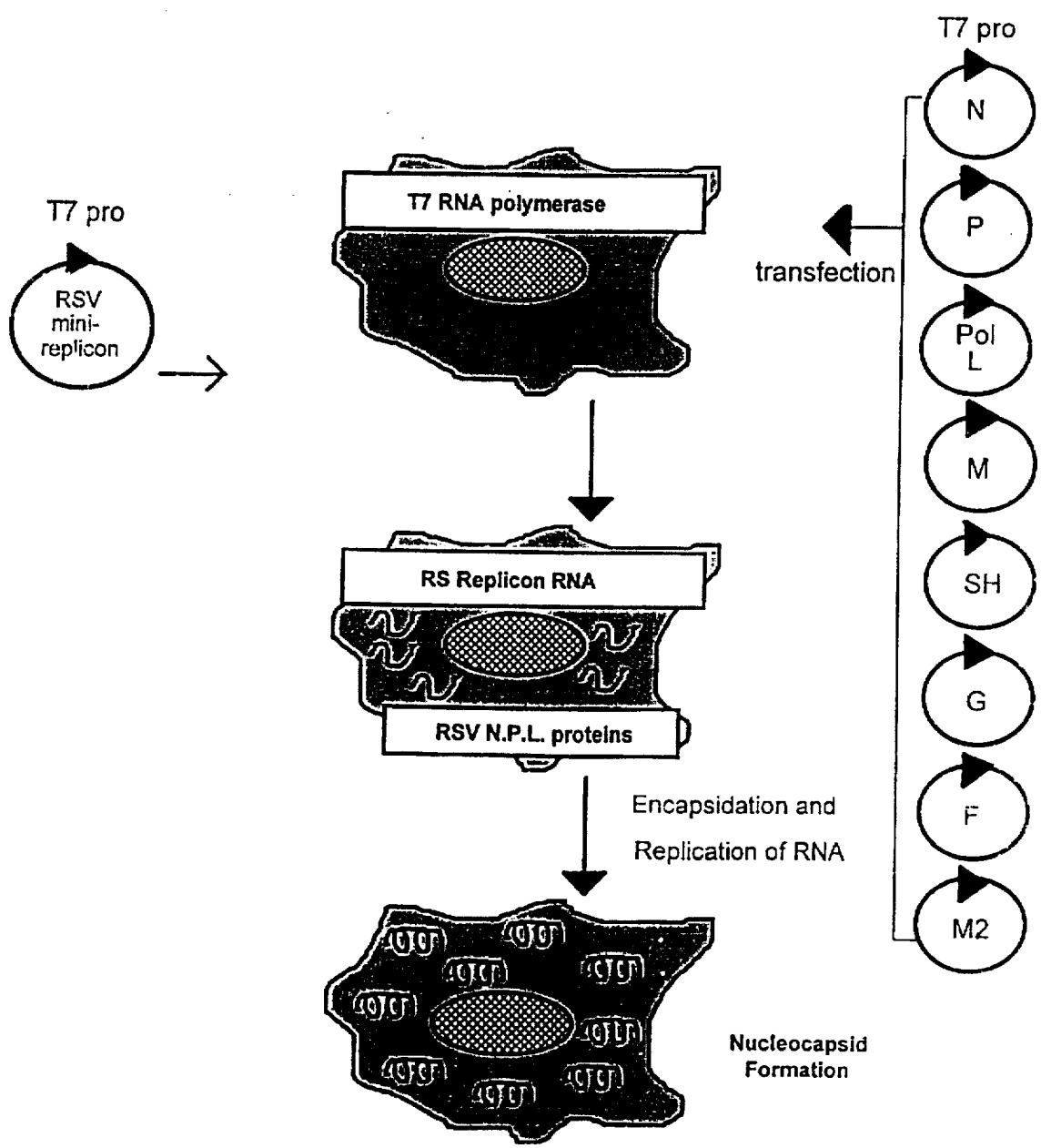

RSV WILD TYPE ANALOGUE
(Mini Replicon)

RSV PANHANDLE ANALOGUE
(Mini Replicon)

PREVENTION AND TREATMENT OF RESPIRATORY TRACT DISEASE

GOVERNMENT SUPPORT

The work resulting in this invention was supported in part by NIH/NIAID Grant No AI20181. The U.S. Government may therefore be entitled to certain rights in the invention.

BACKGROUND OF THE INVENTION

The paramyxovirus human respiratory syncytial virus (hRSV), also known as "pneumovirus", is the major viral cause of respiratory disease (e.g. bronchiolitis and pneumonia) in infants and children. Similarly, bovine respiratory syncytial virus (bRSV) causes bronchiolitis and pneumonia in cattle.

Although infectious respiratory disease caused by hRSV infection is responsible for an estimated 2.2 million human deaths annually, the majority in infancy (Pringle, C. R. (1991) *Bulletin of the Worm Health Organization* 65:133–137), and bRSV epidemics in cattle (particularly in winter) are of economic significance to the beef industry (Bohlender, R. E., et al., (1982) *Mod. Vet. Pract.* 63, 613–618; Stott, E. J. and G. Taylor, (1985) *Arch. Virol,* 84, 1–52; Stott, E. J., et al., (1980) *J. Hyg.* Vol. 85, 257–270), no effective vaccine against hRSV or bRSV is yet available.

This unfortunate situation is compounded by the fact that maternal antibodies do not confer solid immunity on neonates (Stott, E. J. et. al., (1987) *Journal of Virology* 60, 607–613) and natural infection affords only partial protection against frequent repeat infections, as immunity to hRSV is complex, involving both antibody and cell-mediated response (Stott, E. J and G. Taylor (1989) Immunity to Respiratory Syncytial Virus p. 85–104. In Immune Responses, Virus Infections and Disease, N. J. Dimmock, and P. D. Minor, (ed.), vol. 27. IRL Press, Oxford).

A disturbing aspect of the immune pathology of hRSV induced respiratory disease was revealed when a formalin inactivated vaccine was tested. Although the vaccine was antigenic and elicited neutralizing antibody, it failed to protect against subsequent infection, and in fact, its use resulted in enhanced frequency and severity of lower respiratory tract disease in children exposed to subsequent reinfection (Fulginiti, V. A. et. al., (1969) *American Journal of Epidemiology* 89, 435–448 and Kim, H et. al., (1969) *American Journal of Epidemiology* 89, 422–434). It is still unclear why the formalin inactivated live virus vaccine failed.

Naturally attenuated RSV vaccines have been prepared (for example by serially passaging virulent respiratory syncytial virus in human diploid lung fibroblasts see U.S. Pat. Nos. 4,122,167 and 4,145,252 to Buynak and Hilleman; and/or by cold-passage or introduction of mutations which produce viruses having a temperature sensitive or cold adapted phenotype see WO 93/21320 to Murphy et. al.). However, attenuated RSV live virus vaccines have proven to be poorly infectious and overall ineffective in the prevention of respiratory syncytial virus mediated disease.

To address this major health problem, work over the past ten years has focused on the molecular biology of hRSV. cDNAs to all of the RS virus mRNAs have been characterized and used to demonstrate that the negative strand RNA genome of the RS virus possesses 10 genes encoding 10 unique polypeptides (Collins, P. L., Huang, Y. T. and G. W. Wertz (1984) *Journal of Virology* 49, 572–578). The possession of 10 genes sets RS virus apart from other paramyxoviruses, which have only six or seven genes. The RS virus genes, proceeding in order from 3' to 5' on the genome are: NS1 and NS2, which encode two non-structural proteins; N, which encodes the nucleocapsid protein; P, the phosphoprotein; M, the matrix protein; SH, a small hydrophobic protein; G, the attachment glycoprotein; F, the fusion protein; 22K, a second matrix-like protein and L, which encodes the RNA-dependent, RNA polymerase.

Based on the identification of RSV genes and encoded proteins, a variety of vaccines have been prepared. For example, U.S. Pat. No. 5,149,650 by Wertz et. al., describes hRSV subunit vaccines comprising recombinant human RSV (rhRSV) structural proteins. U.S. Pat. No. 5,223,254 by Paradiso et. al., describes rhRSV subunit vaccines comprising polypeptides related to a neutralizing epitope, a fusion epitope, or both, of RS virus glycoproteins, including the F and/or G protein of hRSV, as well as viral vaccines encoding the polypeptides. U.S. Pat. No. 5,288,630 by Wathen et. al., describes vaccines made from DNA viruses such as vaccinia expressing an FG rhRSV chimeric protein. However, none of the currently available vaccines have proven to be both safe and effective at immunizing a subject against RSV infection.

Recombinant DNA techniques (e.g. site specific mutagenesis) offers the possibility of designing highly effective vaccines based on RSV whole viral genomes. However, the RNA of negative stranded viruses is not by itself competent to initiate infection or replication (Huang, Y. T., Collins, P. L. and G. W. Wertz (1985) *Virus Research* 2, 157–173). In virions or intracellularly, RSV RNA is always found tightly encapsidated in a ribonucleoprotein core. This nucleocapsid provides the proteins necessary for transcription and replication and is the minimal unit of infectivity.

Although one group has used recombinant techniques to clone synthetic RSV particles (Collins, P. L., et. al., (1991) *Proc. Natl. Acad. Sci. USA* 88, 9663–9667), wild type hRSV helper virus was used to provide the proteins required for transcription and replication. Contamination by the wild type helper virus, however, makes this method unsuitable for RSV vaccine preparations. In addition, this system works at low efficiency, so that a reporter gene or strong positive selection is required to detect expression from a virus containing the rescued RNA.

The inventors and co-workers have described a method for cloning a defective interfering particle of vesicular stomatitis virus (VSV), another negative stranded RNA virus, that does not require the presence of wildtype helper virus (Pattnaik, A. K. et. al., (1992) *Cell* 69:1011–1020). However, the fact that this method was successful in cloning the relatively small cDNA encoding the defective interfering particle (2.2 kb), does not mean that the method will be equally successful in cloning the much larger cDNAs encoding the RSV genome (at least 15 kb). In addition, use of a similar method for cloning RSV, would require a functional clone of the RSV polymerase (L) gene. Assembly of such a large gene (6578 nt) (Stec, D. S. et. al., (1991) *Virology* 183, 273–287) from a cDNA is, however, vulnerable to the high error rate of the virus RNA-dependent RNA polymerase (estimated at $10^{-3}$ to $10^{-4}$) (Steinhauer, D. A., et. al., (1989) *Journal of Virology* 63,2063–2071), which generates the L mRNA from which the cDNA clones are prepared.

A means for generating recombinant respiratory syncytial virus particles that are not contaminated by wild type helper virus would be useful for producing safe and effective vaccines against respiratory syncytial virus infection, and gene therapy vectors, which are particularly infective in respiratory tract tissue.

SUMMARY OF THE INVENTION

In one aspect, the invention relates to recombinant methods for recovering wildtype or engineered negative stranded, non-segmented RNA virus genomes containing non-coding 3' and 5' regions (.e.g. leader or trailer regions) surrounding one, several or all of the genes of the virus or one or more heterologous gene(s) in the form of ribonucleocapsids containing N, P and L proteins, which are capable of replicating and assembling with the remaining structural proteins to bud and form virions. In one embodiment, the negative stranded, non-segmented RNA virus is the respiratory syncytial virus (RSV) and pure, recombinant, infectious viral particles are made by infecting an appropriate host cell which expresses (or is engineered to express): i) a functional RSV RNA dependent RNA polymerase (L) protein, ii) a functional RSV nucleocapsid (N) protein, and iii) a functional RSV phosphoprotein (P) protein; with an RSV minireplicon, so that the RSV RNA is replicated and encapsidated to form infectious RSV particles. In a preferred embodiment, the functional RSV L, N and P proteins are expressed from plasmids.

In another aspect, the invention features pure, recombinant, non-segmented virus particles, which can be formulated, for example, as vaccines, gene therapy vectors or anti-viral agents. In one embodiment, the non-segmented virus particles are capable of budding and comprise: i) a non-segmented viral RNA dependent RNA polymerase (L); ii) a non-segmented viral phosphoprotein (P), iii) a non-segmented viral nucleocapsid (N), iv) necessary vital structural proteins, v) a 3' non-coding RNA sequence, vi) a 3' to 5' RNA coding region; and vii) a 5' non-coding RNA sequence. Since these particles can infect cells, replicate their genome, transcribe encoded gene(s), and produce and assemble budded infectious particles, they are useful as sustained, non-virulent vaccines or gene therapy vectors. In one preferred embodiment, the non-segmented virus is a respiratory syncytial virus (RSV) and the particles are formulated as vaccines to express antigenic RSV epitopes and thereby confer immunity of a host to respiratory syncytial virus infection. In another preferred embodiment, RSV particles are formulated as gene therapy vectors capable of specifically infecting respiratory tract tissue and expressing therapeutic proteins.

In another embodiment, the non-segmented virus particles comprise: i) a non-segmented virus L protein; ii) a non-segmented virus P protein, iii) a non-segmented virus N protein, iv) necessary viral infection proteins, v) a 3' non-coding RNA sequence, vi) a 3' to 5' RNA coding region; and vii) a 5' non-coding RNA sequence. These particles can infect cells, replicate their genome and transcribe encoded gene(s), which can then be expressed in that cell. However, because they do not comprise necessary structural proteins, the particles are incapable of budding off virions. These particles are particularly useful as vaccines or gene therapy vectors in applications where it is desirable to control (limit) expression of encoded genes (e.g. antigenic or therapeutic proteins or peptides) by controlling the number of cells infected.

In a further embodiment, the non-segmented virus particles are defective interfering particles comprising: i) a non-segmented virus L protein; ii) a non-segmented virus P protein, iii) a non-segmented virus N protein, iv) a 3' non-coding RNA sequence, v) a 3' to 5' RNA coding region and vi) a 5' non-coding RNA sequence. These defective interfering particles can outcompete wild type virus for proteins required for transcription and replication and therefore can be administered to a subject as an antiviral agent.

In still yet another aspect, the invention features a novel cDNA encoding a functional RSV, RNA dependent, RNA polymerase (L) protein. This cDNA has utility not only in generating recombinant RSV particles, but also in drug screening assays to identify drugs that specifically inhibit or interfere with RSV L protein function and that therefore would be highly effective antiviral therapeutics for treating respiratory syncytial virus infection.

Recombinant, non-segmented virus particles made as described herein are not contaminated by helper virus. In addition, the particles can efficiently infect respiratory tract tissue. Further, various types of particles can be formulated, depending on the intended use. For example, "budding" recombinant, non-segmented virus particles can be formulated and used as vaccines or gene therapy vectors, where widespread and sustained expression of antigenic or therapeutic proteins is desired. Alternatively, "non-budding" non-segmented virus particles can be used as vaccines or gene therapy vectors, where limited or controlled expression of antigenic or therapeutic proteins is desired. Defective interfering virus particles can be used as anti-viral agents to interfere and prevent replication of wild-type virus. Other features and advantages will be readily apparent from the following detailed description and claims.

BRIEF DESCRIPTION OF THE DRAWINGS

FIG. 2 is a diagrammatic representation of a process for generating pure, infectious and budding RSV particles.

DETAILED DESCRIPTION OF THE INVENTION

Figure 1:
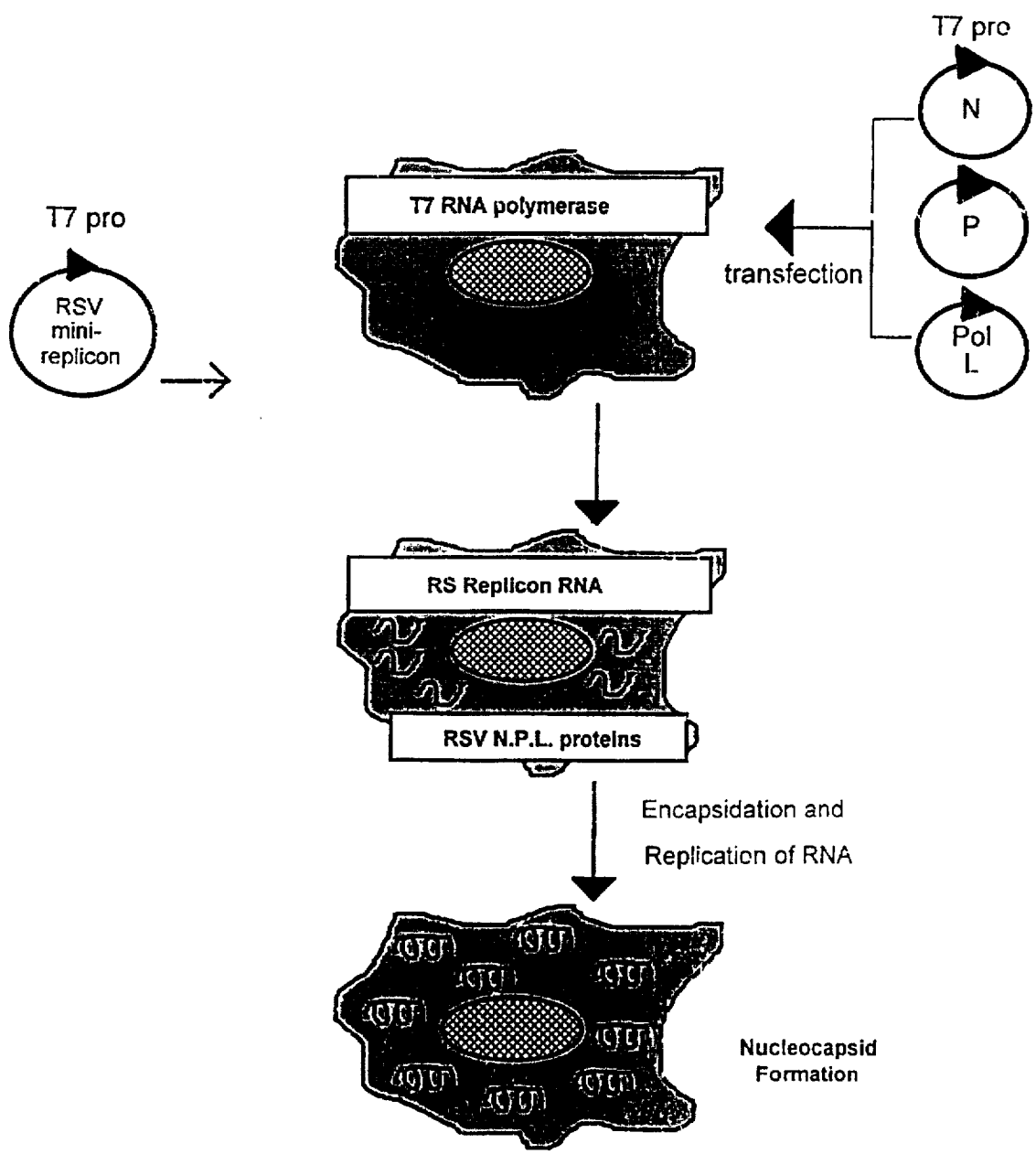
FIG. 1 is a diagrammatic representation of a process for generating pure, RSV ribonucleoprotein (RNP) particles.
Figure 3:
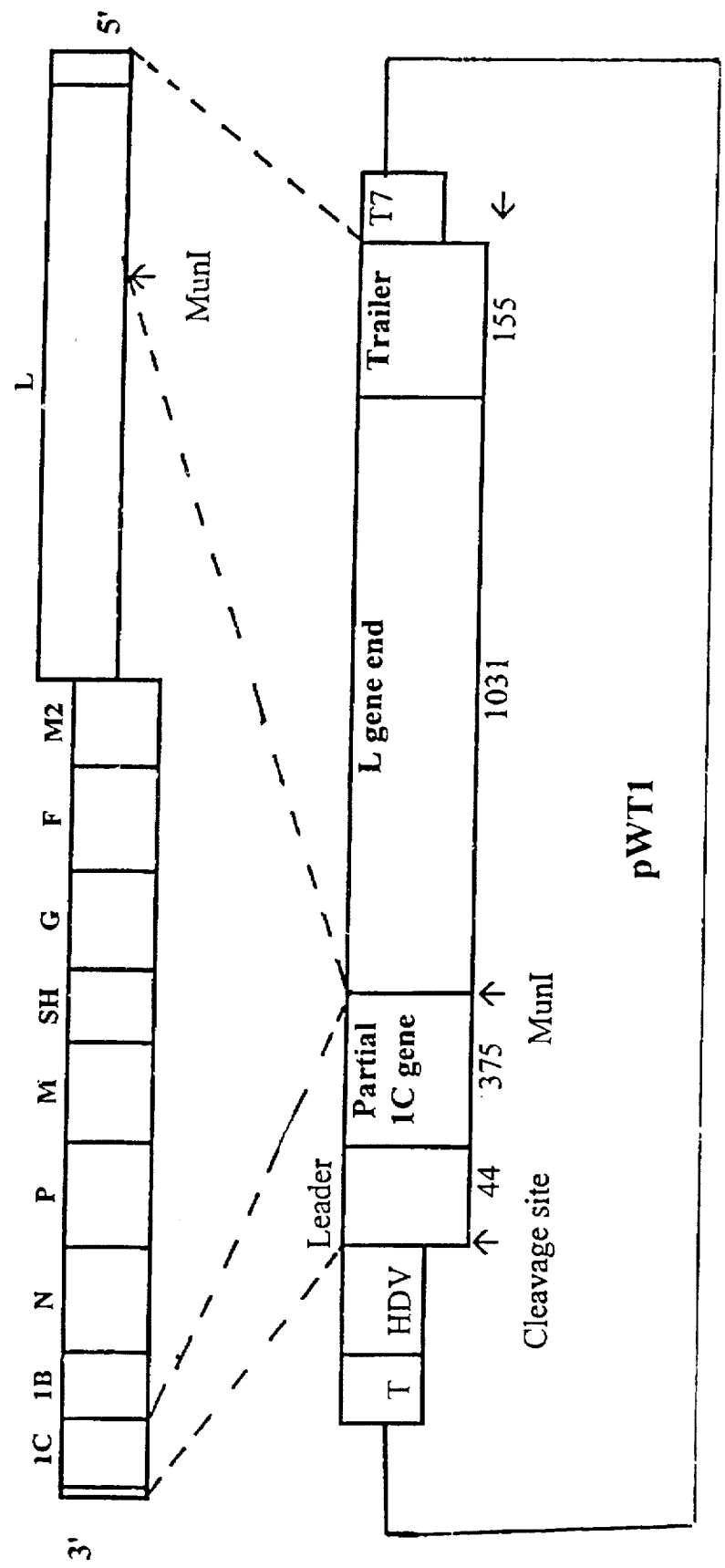
FIG. 3 is a diagrammatic representation of an RSV cDNA wildtype minireplicon.

The instant invention is based on the identification of cDNA encoding a novel, functional respiratory syncytial virus (RSV) RNA dependent RNA polymerase and use of the cDNA for recovering wildtype or engineered RSV RNA genomes containing the 3' leader and 5' trailer or combinations thereof surrounding one, several or all of the genes of the virus or one or more heterologous gene(s) in the form of ribonucleocapsids containing the RSV N, P and L protein which are capable of replicating and assembling with the remaining structural proteins to bud and form virions. Because of the common mechanism of replication, transcription, assembly and budding, similar methods can be used to recover other wild-type or engineered non-segmented, negative stranded RNA viral genomes.

Non-segmented Negative Stranded RNA Viruses

Virus families containing enveloped, single-stranded, negative sense (3' to 5') RNA are classified into groups having non-segmented genomes (Paramyxoviridae, Rhabdoviridae) or those having segmented genomes (Orthomyxoviridae, Bunyaviridae and Arenaviridae).

Of the non-segmented viruses, the Rhabdovirus family includes the vesiculovirus (e.g. vesicular stomatitis virus (VSV)) and the lyssavirus (e.g. rabies) genuses. The Paramyxovirus family includes the morbillivirus (e.g. measle virus), the paramyxovirus (e.g. sendai virus; human parainfluenza virus types 1, 2 and 3; mumps virus; simian virus type 5; and newcastle disease virus) and the pneumovirus (e.g. respiratory syncytial viruses (RSV), pneumovirus of mice and turkey rhinotracheitis virus) genuses.

RSV have been isolated from a number of mammals including chimpanzee (Morris, J. A., et al., (1956) *Proc. Soc. Exp. Biol. Med*, 92, 544–549); humans (Lewis, F. A., et al., (1961) *Med J. Aust.*, 48, 932–933); cattle (Paccaud, M. F. and C. Jacquier, (1970) *Arch. Gesamte Virusforsch*, 30, 327–342); sheep (Evermann, J. F., et al., (1985) *Am. J. Vet. Res.*, 46, 947–951); and goats (Lehmkuhl, H. D., et al., (1980) *Arch. Virol.*, 65, 269–276). Human RSV (hRSV) have been classified into two subgroups A and B, which include a number of strains (e.g. A2 and 18537). A number of strains of bovine (bRSV) have also been indentified (e.g. A51908 and 391-2).

hRSV genomic RNA is approximately 15.2 kb in length. Transcription of the genome initiates at the 3' extracistronic region and proceeds in a sequential polar fashion to yield 10 mRNAs each encoding a major polypeptide. The hRSV genome also has a 44 nucleotide (nt) leader at the 3' end and a 155 nt noncoding trailer sequence at the 5' end (Mink M. A., et al., (1991) *Virology* 185, 615–624. Proceeding from 3' to 5' on the genome, wild type hRSV includes the following 10 genes: NS1 and NS2 (also referred to as 1C and 1B), which encode two non-structural proteins; N, which encodes the nucleocapsid protein; P, the phosphoprotein; M, the matrix protein; SH, a small hydrophobic protein; G, the attachment glycoprotein; F, the fusion protein; 22K, a second matrix-like protein and L, which encodes the RNA-dependent, RNA polymerase.

Complete nucleotide sequences have been determined for the nine smaller RSV genes (Collins, Peter L., (1991) *The Molecular Biology of Human Respiratory Syncytial Virus (RSV) of the Genus Pneumovirus* in The Viruses, Frankel Conrat & Kobert Wagner (ed. David Kingsbury Plenum, New York; Collins, P. L. et. al., (1991) *Proc. Natl. Acad. Sci. USA* 88:9663–9667; Sullender, W. M. et. al., (1991) *J. of Virology* 65: 5425–5434; Sullender, W. M. et. al., (1990) *Virology* 178:195–203; Collins, P. L. and G.W. Wertz, (1985) *Virology* 141:283–291; P. L. Collins and G. W. Wertz, (1985) *J. of Virology* 54:65–71; Collins, P. L. and G. W. Wertz (1985) *Virology* 143:442–451; Collins, P. L. et. al., (1985) *Virology* 146: 69–77; Collins, P. L. et. al., (1984) *J. of Virology* 49: 572–578; Satake, M. et. al., (1984) *Journal of Virology* 52: 991–994; Collins, P. L. and G. W. Wertz (1983) *Proc. Natl. Acad. Sci. USA* 80: 3208–3212. In addition, a functional cDNA encoding functional RNA-dependent RNA polymerase was identified as described in Example 1.

The bRSV genome encodes 10 proteins that correspond closely in size to the hRSV proteins (Lerch, R. A., (1989) *Journal of Virology*, 63, 833–840). Complete nucleotide sequences have been determined for the N (Amann, V. L., (1992) *Journal of General Virology*, 73 999–1003); F (Lerch, R. A., et al., (1991) *Virology*, 181, 118–131) and G (Lerch, R. A. et al., (1990) *Journal of Virology*, 64, 5559–5569) proteins. cDNA clones corresponding to 9 of the 10 bRSV mRNAs (all but the L protein) have been constructed (Lerch, R. A. et al., (1989) *Journal of Virology*, 63, 833–840.

Recovering Wildtype or Engineered Non-segmented Negative Stranded RNA Viruses In general, pure, infectious RSV particles can be generated by introducing a cDNA "minireplicon" into a host cell which minimally contains the following functional proteins: i) a non-segmented virus RNA dependent RNA polymerase (L) protein ii) a non-segmented virus nucleocapsid (N) protein; and iii) a non-segmented virus phosphoprotein (P). Preferably, genes encoding the non-segmented virus L, N, and P proteins have been introduced into the host cells as plasmids under the control of a promoter region that is recognized by a DNA dependent RNA polymerase. The DNA dependent RNA polymerase can be native to or engineered into the host cell.

FIG. 1 is a diagrammatic representation of a process for generating pure, infectious RSV ribonucleoprotein (RNP) particles, which are capable of infection, but not of budding virions. Additional proteins for facilitating infection, "infection proteins", such as RSV F and G proteins, can be incorporated into host ceils in the same manner that non-segmented virus N, P, and L proteins are supplied. A preferred method for making these particles is described in detail in the following Example.

In order to make particles that are capable of budding and forming progeny virions, non-segmented virus structural proteins must also be expressed in a host cell. Preferred RSV structural proteins are selected from the group consisting of RSV N,P,M,M2,SH,G or F proteins. FIG. 2 is a diagrammatic representation of a process for generating pure, infectious and budding non-segmented viral particles.

As shown in FIGS. 1 and 2, in a preferred method, cDNA encoding the T7 RNA polymerase is introduced into a host cell using the vaccinia virus-T7 RNA polymerase expression system (Fuerst, T. R. et al., (1986) *Proceedings of the National Academy of Sciences USA* 83, 8122–8126). Plasmids encoding functional proteins (N, P and L) alone (FIG. 1) or in conjunction with structural proteins (FIG. 2) under the contol of the T7 polymerase are then transfected into the host. Minireplicons under the control of the same T7 polymerase are also transfected into the host cell.

The T7 RNA polymerase transcribes the functional proteins, structural proteins (if present) and minireplicon cDNA into replicon RNA transcripts with precise termini, which are replicated and encapsidated to form nucleocapsids. Preferably the replicon RNA trascripts are in the presence of a pool of nucleocapsid protein (i.e. N and P in approximately the same molar ratio) such that encapsidation of the nascent RNA can begin immediately, thereby enhancing the chances of success.

FIGS. 3 and 4 provide diagrammatic representations of RSV minireplicons; wildtype (FIG. 3) and panhandle (FIG. 4). For use in the invention, a minireplicon must include: i) a 3' non-coding RNA sequence, ii) a 3' to 5' RNA coding sequence, and iii) a 5' non-coding sequence. The 3' and 5' non-coding RNA sequences are essential to replication by a non-segmented viral polymerase. As shown in FIGS. 3 and 4, the 5' non-coding sequence can be a trailer sequence (e.g. the RSV 155 nucleotide trailer sequence) and the 3' non-coding sequence can be a leader sequence (e.g. the RSV 44 nucleotide trailer sequence). In general, polymerases of non-segmented viruses are specific to their own leader and trailer sequence.

The replicons shown in FIGS. 3 and 4 employ three basic elements for ensuring intracellular transcription of RNAs with precise termini. A truncated form of the bacteriophage T7 promoter (Tϕ) immediately followed by a multiple cloning site with two blunt-ended restriction sites. The promoter distal site is immediately followed by a cDNA copy of the autolytic ribozyme from the antigenomic strand of hepatitis delta virus (HDV) which, in turn, is immediately followed by a T7 terminator element (Tϕ). Transcription by the T7 polymerase yields an RNA with two additional nucleotides at the 5' end of the transcript, continuing through the ribozyme and terminating in the Tφ terminator sequence. A precise 3' terminus is generated by the autolytic cleavage of the primary transcript by the HDV genomic RNA at the exact terminus of the RS virus genomic insert.

In between the 3' and 5' non-coding RNA sequences, a minireplicon contains a 3' to 5' RNA coding region, which can encode, for example non-segmented viral genes or foreign proteins (e.g. therapeutic or diagnostic proteins). Each gene encoded in a minireplicon must have appropriate transcription start and stop signals and intracistronic junctions to signal transcription by the polymerase and subsequent translation to yield protein. Theoretically, there is no limit in the amount of RNA that can be included in the 3' to 5' coding region. In practice, the size of the coding cDNA will be limited by the amount that can be replicated.

In the system described in the Example, the quantity of viral-like RNA transcribed is equivalent to the amount of 28 and 18S fibosomal RNA concurrently synthesized in the cell between 12 to 20 hours post-transfection. From five to ten percent of the total RNA transcribed can be selectively encapsidated. In addition, the encapsidated RNA can be replicated if the termini of the transcript are exact (Pattnaik, A. K. et. al., (1992) Infectious defective interfering particles of VSV from transcripts of a cDNA clone. *Cell* 69:1011–1020). The limiting factor in encapsidation appears to be the amount of nucleocapsid (N) and (P) proteins that can be synthesized.

Eukaryotic cells are preferable "host cells" for producing non-segmented viral particles in vitro. Prokaryotic cells may also be used, but would likely require modification to generate appropriately glycosylated particles. Preferred host cells are mammalian cell lines which are capable of being infected by a non-segmented virus (e.g. HEp-2, HeLa, thymidine kinase deficient (tk-) cells, human embryonic diploid fibroblast, primary monkey or calf kidney cells, human embryonic kidney, COS, C127, baby har ster kidney (BHK), Vero, LLCMK-2, BSC-1, CV-1,293.

As an alternative to production of non-segmented viral particles by in vitro culture, the particles can also be produced in vivo, for example by introducing appropriate expression systems into an animal host having cells that are capable of being infected by the virus and contain (or have been engineered to contain) functional, non-segmented virus L, N and P proteins.

Introduction of minireplicons into a host cell can be accomplished using standard techniques (e.g. via viral infection, calcium phosphate or calcium chloride co-precipitation, DEAE dextran mediated transfection, lipofection or electroporation). A preferred method of introduction is described in Fuerst, T. R. et. at., (1987) Use of a Vaccinia Virus T7 RNA Polymerase System for Expression of Target Genes. *Mol. Cell. Biol.* 7:2538–44. Recombinant cells expressing the infectious viral particles can be cultured in vitro and the particles can be purified using well-known techniques.

Vaccines

Respiratory synctial virus is the major viral cause of respiratory disease (e.g. bronchiolitis and pneumonia) in infants and children. Using the above-described system for replicating pure populations of infectious RSV particles, a variety of vaccines can be prepared and tested for ability to induce an immune response (against RSV or any other non-segmented negative stranded RNA virus) in a subject. The 3' to 5' coding region of appropriate vaccine candidates will encode at least one RSV protective epitope (i.e. an epitope that elicits an immune response in a subject. For example, an epitope may be from an RSV N, P, M, SH, G, F or 22K protein. Particularly preferred protective epitopes express a protective epitope of the G glycoprotein, which is thought to mediate attachment of the virus to the host cell and/or the F (fusion) glycoprotein, which is thought to be responsible for virus penetration and fusion of infected cells with contiguous cells to produce syncytia.

Alternatively, particles expressing a RSV protective epitope can be used to infect an appropriate host cell (in vitro or in vivo) for production of recombinant RSV protective epitopes, which can then be formulated into a "subunit vaccine".

An "effective amount" of live-virus or subunit vaccine prepared as disclosed herein can be administered to a subject (human or animal) alone or with an adjuvant (e.g. as described in U.S. Pat. No. 5,223,254 or Stott et al., (1984) *J. Hyg. Camb.* 251–261) to induce an active immunization against RSV infection. An effective amount is an amount sufficient to confer immunity against RSV and can be determined by one of skill in the art using no more than routine experimentation. Determination of an effective amount may take into account such factors as the weight and/or age of the subject and the selected route for administration.

A cocktail of infectious virus particles expressing different RSV protective epitopes can also be prepared as a vaccine composition. Vaccines can be administered by a variety of methods known in the art. Exemplary modes include oral (e.g. via aerosol), intradermal, intramuscular, intraperitoneal, intravenous, subcutaneous, parental, transdermal and intranasal routes. If necessitated by a particular mode, the vaccine may be encapsulated.

Gene Therapy Vectors

Natural respiratory syncytial virus specifically infects respiratory tract tissue (e.g. lung epithelia). Based on this natural affinity, the non-segmented viral particles disclosed herein can be used as gene therapy vectors by engineering the 3' to 5' coding region to encode a protein (e.g. a therapeutic or diagnostic protein, peptide or polypeptide) or nucleotide (e.g. oligonucleotide, e.g. for antisense therapy) for delivery to a subject's respiratory tract. In a preferred embodiment, the protein has bioactivity in a subject's lung. In a particularly preferred embodiment, the protein is selected from the group consisting of: the cystic fibrosis transmembrane conductance regulator (CFTR) protein or a functional fragment thereof, an anti protease (e.g. alpha-1-antitrypsin), a tissue inhibitor of metaloproteinase, an antioxidant (e.g., superoxide dismutase), a cytokine (e.g., an interferon), a mucolytic (e.g., DNase); or a protein which blocks the action of an inflammatory cytokine.

An "effective amount" of a gene therapy vector prepared from a non-segmented viral particle can be administered to a subject (human or animal). An effective amount is an amount sufficient to accomplish the desired therapeutic or diagnostic effect and can be determined by one of skill in the art using no more than routine experimentation. Determination of an effective amount may take into account such factors as the weight and/or age of the subject and the selected route for administration.

Gene therapy vectors can be administered by a variety of methods known in the art. Exemplary modes include oral (e.g. via aerosol), intradermal, intramuscular, intraperitoneal, intravenous, subcutaneous, parental, transdermal and intranasal routes. If necessitated by a particular mode, the gene therapy vector may be encapsulated.

In addition to being prepared as a gene therapy pharmaceutical, the infectious particles can be used to infect an appropriate host cell to produce the recombinant protein in vitro (e.g. in a cell culture) or in vivo (e.g. in a transgenic animal).

Anti-viral Agents

Defective Interfering Particles

Defective interfering (DI) particles are subgenomic virus particles (lacking greater or lesser percentages of the virus genome). They contain virus structural proteins and antigens. DI particles require homologous parental (wildtype) virus for replication and replicate preferentially at the expense of helper virus, thereby causing interference. Defective interfering particles can also enhance interferon production, modulate surface expression of viral proteins, affect their transport, processing and turnover, and alter the timing and basic pathology of a virus infection in vivo (Holland, John J., *Defective Interfering Rhabdoviruses*, Dept. of Biology, University of California at San Diego, La Jolla, Calif. 92093, Chapter 8, pp. 297–360).

Figure 4:
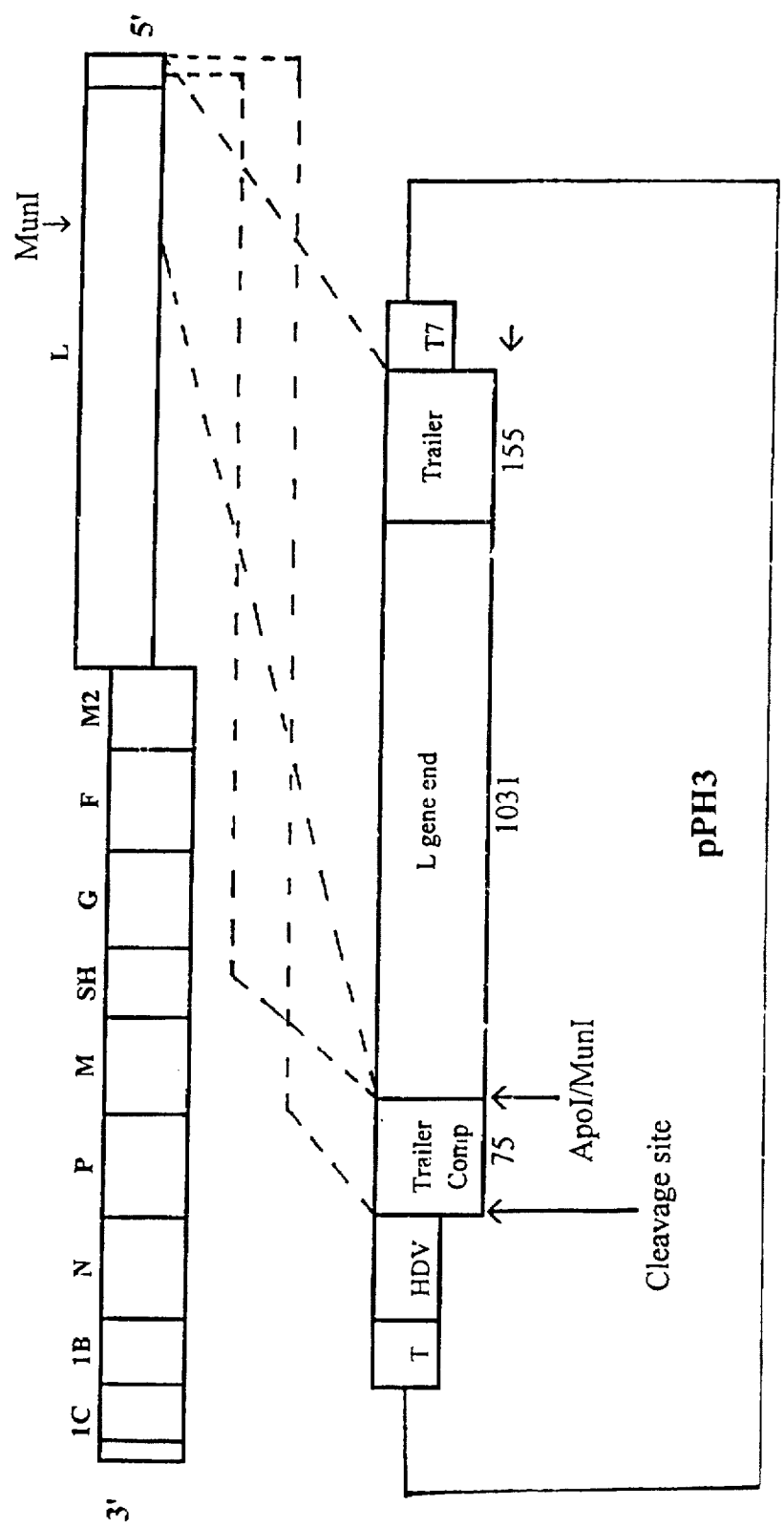
FIG. 4 is a diagrammatic representation of an RSV cDNA panhandle minireplicon.

As described in detail in the following Example, defective interfering particles have been made using the panhandle RSV minireplicon shown in FIG. 4. The panhandle construct contains an authentic 5' terminus and its complement at the 3' terminus as found in copy-back DI RNAs of other negative strand viruses. These defective interfering particles can outcompete wild type virus for proteins required for transcription and replication and therefore can be administered to a subject as an antiviral agent.

Other DI particles essentially comprising: i) a non-segmented virus L protein; ii) a non-segmented virus P protein, iii) a non-segmented virus N protein, iv) a 3' non-coding RNA sequence, v) a 3' to 5' RNA coding region and vi) a 5' non-coding RNA sequence can be designed. Preferable DI particles, (i.e. DI particles with the greatest replicative advantage) maximize the extent of terminal complementarity between the 3' and 5' non-coding sequences. Work with a copy-back family of VSV DI particles, has shown that the extent of complementarity, rather than their exact sequence, is a major determinant of whether a template predominantly directs transcription or replication (Wertz, G. et al., (1994) *Proc. Natl. Acad. Sci. USA*, 91, 8587–8591).

Drug Screening

Effective antiviral drugs specifically prevent or neutralize viral infectivity without affecting host cells. Because the RNA dependent RNA polymerase performs a function unique to negative stranded RNA viruses, a drug that could interfere with the function would be a useful therapeutic against RSV mediated disease. Host cells expressing RSV RNA dependent RNA polymerase as described herein can be used as screens to test various drug candidates for anti-respiratory syncytial virus activity. For example, one can infect cells with VVTF7-3, transfect in the plasmids for N,P,L and suitable RSV mini genomes and measure the effect of drugs on RSV specific RNA replication and transcription, for example, using suitable radiolabelling techniques. This could be accomplished as a screen in cells in culture.

An "effective amount" of an antiviral compound, such as a defective interfering particle or drugs specifically interfering with the replication or transcription of a non-segmented virus, can be administered to a subject (human or animal).

An effective amount is an amount sufficient to alleviate or eliminate the symptoms associated with viral infection. The effective amount for a particular antiviral agent can be determined by one of skill in the art using no more than routine experimentation. Determination of an effective amount may take into account such factors as the weight and/or age of the subject and the selected route for administration.

Antiviral agents can be administered by a variety of methods known in the art. Exemplary modes include oral (e.g. via aerosol), intradermal, intramuscular, intraperitoneal, intravenous, subcutaneous, parental, transdermal and intranasal routes. If necessitated by a particular mode, the gene therapy vector may be encapsulated.

The present invention is further illustrated by the following examples which should not be construed as limiting in any way. The contents of all cited references (including literature references, issued patents, published patent applications, and co-pending patent applications) cited throughout this application are hereby expressly incorporated by reference.

EXAMPLE

Functional cDNA Clones of RSV N, P and L Proteins Support Replication of RSV Genomic RNA Analogs and Define Minimal Trans-acting Requirements for Replicating Materials and Methods Construction of Full Length cDNAs Encoding the RS Virus N, P and L Proteins All procedures and reaction conditions for plasmid constructions were carried out according to standard methods (Sambrook et al., (1989) Molecular Cloning: A Laboratory Manual, Cold Spring Harbor Laboratory Press, Cold Spring Harbor, N.Y.). The plasmid constructs were verified by DNA sequence determination of the relevant regions by the dideoxy chain termination method using denatured plasmid DNA as templates (Haltiner, M. et al., (1985) *Nucleic Acids Research* 1015–1028).

In order to express RS virus proteins in the VVT7 based reverse genetic analysis system, cDNA clones of the RS virus N, P and L genes were cloned into pGEM3 vectors downstream of T7 RNA polymerase promoter, the clones were designated pRSV-N, pRSV-P and pRSV-L, respectively. Briefly, pRSV-N was prepared by transferring a BamHI-PstI fragment containing the entire N gene from pAQ330 (King et al., (1987) *Journal of Virology* 61, 2885–2890) into a pGEM3 vector. cDNA encoding the P protein was generated by reverse transcription of RS virus genomic RNA, followed by PCR amplification with a pair of oligo nucleotide primers corresponding to nt positions 2328–2349 and 3459–3443 of the genome (Galinski 1991), respectively. The cDNA was then cloned into the KpnI-BamHI site of pGEM3. Because of the size of the L gene, (6,578 nt, Stec et al., (1991) *Virology* 183, 273–287), the full-length L gene clones were constructed through several steps of subcloning and finally by assembling four exchangeable segments. Segment 1 (KpnI-MspI fragment, positions 1-1906 in the L gene), segment 2 (MspI-PflMI fragment, positions 1907–3795) and segment 4 (MunI-PstI fragment, positions 5547–6732) were prepared by reverse transcription and PCR amplification, using three pairs of oligo nucleotide primers corresponding to nt positions 1–17 and 1923–1903, 1881–1902 and 3802–3788, and 5420–5441 and 6732–6700 of the L gene, respectively. Segment 3(PflMI-MunI fragment) came from an existing clone pRSVL-35 which was prepared by oligo-dT primed cDNA synthesis (Collins and Wertz (1983) *Proceedings of the National Academy of Sciences, USA* 80, 3208–3212). The originally assembled clone yielded a 170 KDa polypeptide on translation. Sequencing analysis revealed that an adenosine residue at nt position 4762 of the L gene had been deleted, resulting in a frame-shift generating a premature stop codon 48 nt downstream of the deletion. This sequence error was repaired by site directed mutagenesis.

Generation of cDNA Clones Encoding RS Virus Genomic Analogs cDNA clones that transcribe two types of RS virus genomic analogs were constructed. The first type (Wild-type) contained the authentic 3' and 5' termini of the genome, but deleted the majority of the internal genes, and the second type (Panhandle-type) contained complementary termini, derived from the 5' terminus of the genome, surrounding a partial L gene. (Diagrams of these two analogs are shown in FIGS. 1 and 2.)

The wild -type analog plasmid (pWT) was prepared as follows: cDNA containing the 3' leader, 1C, 1B, N and part of P genes was synthesized by reverse transcription and followed by PCR amplification with a pair of oligo nucleotide primers corresponding to nt positions 1–29 and 2378–2360 of the genome. A 2.3 kb PCR product was cloned into the KpnI-SalI site of pGEM3, and the resulting plasmid was digested with SacI and MunI to release a 0.4 kb fragment containing the 3' 44-nt leader and nucleotides 1–375 of the 1C gene. Consequently, this SacI-MunI fragment was fused with a MunI-PstI fragment containing nucleotides 5547–6578 (1031-nt) of the L gene and 155-nt trailer, which was derived from pRSV-L, and cloned into pGEM3. The resulting clone was digested with BsiWI and the termini of the released 1.6 kb BsiWI fragment repaired by partial filling with dGTP, dTTP, Klenow (BRL), followed by mung bean nuclease digestion. This generated a blunt-ended DNA fragment whose terminal sequences precisely matched the authentic termini of the RS virus genome. This fragment was then inserted into the SmaI site of a transcription plasmid between the T7 promoter and the antigenomic-strand of hepatitis delta virus (HDV) autolytic ribozyme followed by T7 terminator sequences (Ball, L. A. et al., (1992) *Journal of Virology* 66, 2335–2345.). In this sequence context, the wild-type RNA analog synthesized by the T7 RNA polymerase was predicted to contain two non RS virus GTP residues at the 5' end and, after autolytic cleavage, an exact terminus corresponding to the authentic genome 3' end.

The panhandle-type analog (pPH) was derived from the trailer region and the L gene end sequences. A 1.2 kb MunI-PstI fragment containing the L gene 5' end and the trailer region was isolated from pRSV-LS4 and fused with an ApoI-PstI fragment comprising 75 nucleotides of the extreme 5' end of the trailer, and subsequently cloned into the PstI site of pGEM3. The resulting clone was treated the same as described in the wild-type analog construction and finally transferred into the SmaI site of the intracellular transcription plasmid. Therefore, the T7 transcripts from the panhandle type analog plasmid were predicted to contain, after autolytic cleavage, complementary 75-nt termini derived from the trailer, surrounding the 1031-nt L gene end.

Virus Infections and DNA Transfections 293 cells were grown in Dulbecco's Modified Eagle Medium (D-MEM, GIBCO Laboratories) containing 10% heat-inactivated fetal bovine serum (FBS) in 60 mm plates. A subconfluent cell monolayer (about $3\times10^6$ cells per plate) was infected with recombinant vaccinia virus vT7-3 (moi of 10 pfu per cell) that expresses T7 RNA polymerase. After 45 minutes virus absorption, the cells were washed once with D-MEM (without FBS) and then transfected with appropriate plasmid DNAs using lipofectin according to manufacturer's (Bethesda Research Laboratories) instructions. For protein expression, the cells were transfected with 5 ug ofpRSV-N, pRSV-P or pRSV-L individually or simultaneously, whereas for RNA replication assay, the cells were transfected with 5 ug of pPH3 or pWT1, and combinations of 5 ug of pRSV-N, 2 ug of pRSV-P and 0.25–2.0 ug of pRSV-L. The transfected cells were then incubated in D-MEM (without FBS) 37° C. for 12–16 hours before labeling with radioisotopes.

Immunoprecipitation and Electrophoretic Analysis of Proteins

For radiolabeling of expressed proteins, at 12 hours posttransfection the cells were incubated in methionine-free medium (GIBCO Laboratories) for 45 minutes and then exposed to $[^{35}S]$ methionine (20 uCi/ml, Du Pont/NEN) for 3 hours. Cytoplasmic extracts of cells were prepared and viral specific proteins were immunoprecipitated as described previously (Pattnaik, A. K. and G. W. Wertz, (1990)*Journal of Virology* 64, 2948–2957) by using goat polyclonal antiserum raised against RS virus (Chemicon International). For detecting expression of the L protein, rabbit antisera raised against the L protein specific peptides (three peptides corresponding to amino acid positions 1696–1713, 1721–1733 and 2094–2110, respectively, Stec et al., (1991) *Virology* 183, 273–287) were synthesized by the UAB Protein Synthesis Core Facility, conjugated to KLH and antiserum raised in rabbit by Lampire Biological Laboratories, Inc. A combination of the anti-L-peptide sera was used for immunoprecipitation of the L protein. Immunoprecipitated proteins were analyzed by electrophoresis on 10% polyacrylamide gels and detected by fluorography as described previously (Pattnaik, A. K. and G. W. Wertz, (1990) *Journal of Virology* 64, 2948–2957).

Analysis of RNA Replication

To analyze RNA replication, cells were exposed to $[^3H]$ uridine (25 uCi/ml, Du Pont/NEN) between 16–24 hours posttransfection, in the presence, where indicated, of actinomycin D (10 ug/ml, water-soluble mannitol complex; Sigma Chemical Co.) after 30 minutes actinomycin D pretreatment. Cells were harvested and cytoplasmic extracts prepared as described previously. Either total RNA or N-protein encapsidated RNA selected by immunoprecipitation with the goat antiserum, was extracted and analyzed by electrophoresis on 1.75% agarose-urea gels and detected by fluorography (Wertz, G. W. and N. Davis (1981) *Nucleic Acids Research* 9, 6487–6503).

RNA Protection Assay of Replication Products

An RNA protection assay (RPA) was used to detect strand-specific RNA synthesis using an RPA II kit according to manufacturer's instructions (Ambion). Briefly, N-protein encapsided RNAs from one 60 mm plate of cells transfected with pPH3 and the N, P or N, P and L protein plasmids as described above (without radiolabeling and actinomycin D treatment) were selectively enriched by immunoprecipitation and were used in RPA for each reaction. A strand-specific RNA probe was generated by T7 RNA polymerase in vitro transcription of a pGEM3 plasmid with incorporation of [$^{35}$S] UTP (Du Pont/NEN) according to the manufacturer's instructions (New England Biolabs). The pGEM3 plasmid containing a BclI-BglII fragment of the L gene end (positions 5655–6514) was linearized by digestion with SspI, the cleavage site for which is present in the BclI-BglII fragment (position 6158), so that run off T7 polymerase transcription produced a 391-nt RNA probe. The RNA probe was purified by polyacrylamide gel electrophoresis. The specific activity of the purified probe was determined and $6\times10^3$ cpm of probe was used in each reaction of the assay. The protected RNA was analyzed by electrophoresis on 4.5% sequencing gels and detected by fluorography.

Results

Expression of RS Virus Proteins

In order to establish a reverse genetic approach for analysis of RS virus, it was necessary to prepare cDNA clones capable of expressing the RS virus proteins involved in RNA replication. By analogy with other negative-stranded RNA viruses, these would most likely be the N, P and L proteins, although at the outset it was unknown whether the nonstructural proteins 1C and 1B might also be required. Full-length cDNA clones of the N, P and L genes were prepared as described and subcloned into the expression vector pGEM3. To detect whether these cDNA clones expressed N, P and L proteins, the recombinant vaccinia virus-T7 RNA polymerase expression system was used. (Fuerst, T. R. et al., (1986) *Proceedings of the National Academy of Sciences USA* 83, 8122–8126). 293 cells were infected with vTF7-3 and transfected with plasmids pRSV-N, pRSV-P, or pRSV-L. At 12 hours posttransfection, the cells were labeled with [$^{35}$S]methionine for 3 hours. Cytoplasmic extracts were prepared, and proteins were immunoprecipitated with anti-RS virus antibody in the case of the N and P proteins, or anti-L-peptide antisera in the case of the L protein, and analyzed by electrophoresis.

vTF7-3 infected cells transfected with pRSV-N expressed a protein which comigrated with the authentic N protein synthesized in RS virus infected cells. Similarly, vTF7-3 infected cells transfected with pRSV-P also expressed a protein which comigrated with the authentic P protein. Neither untransfected nor uninfected cells produced these proteins, suggesting that pRSV-N and pRSV-P expressed the appropriate viral proteins.

A cDNA clone containing the L gene constructed as described above was transfected into vTF7-3 infected cells. The total expressed products were analyzed by SDS-PAGE and a polypeptide with a molecular weight of 170 kDa was observed, but not the expected 250 kDa polypeptide. Sequencing analysis revealed that an adenosine residue at nt position 4762 of the L gene had been deleted, resulting in a frame-shift which generated a premature stop codon 48 nt downstream of the deletion. The sequence error was repaired by restoring the A residue by site-directed mutagenesis. A corrected L gene cDNA clone was constructed and expressed in the same system. In order to detect the L protein, rabbit anti-L-peptide sera were prepared and used to immunoprecipitate the products of expression. The results showed that a polypeptide of 250 Kd expressed from the repaired L gene clone was identified by the anti-L-peptide sera, which comigrated with the authentic L protein. A few faint bands migrating faster than the L protein were also observed, which might be the products derived from late initiations of translation, or degradation of the L protein. This work demonstrated that the corrected full-length L gene clone was capable of directing synthesis of authentic size RS virus L protein. Consequently, this cDNA clone was used in RNA replication experiments to test whether the expressed L protein was a functional polymerase.

Expression of Genomic RNA Analogs

To establish the reverse genetic analysis system, cDNA clones that transcribed two types of RS virus genomic RNA analogs were constructed. As shown in FIG. 1, the wild-type cDNA clone, pWT1, encoded an analog of RS virus genomic RNA in which the majority of the internal genes were deleted. Transcription of pWT1 by T7 RNA polymerase would yield a 1605-nt long, negative-sense RNA with the authentic 3' terminus of the RS virus genome, created by the autolytic cleavage of the ribozyme, and the following structural features (listed in 3' to 5' order): (i) the 44-nt leader region; (ii) nt 1–375 of the 1C gene; (iii) nt 5547–6578 (1031-nt) of the L gene; (iv) the 155-nt trailer region and (v) two non RS virus GTP residues encoded by the vector. Similar to pWT1, the panhandle-type cDNA clone, pPH3, encoded an RS virus genomic analog in which most of the internal genes had been deleted.

However, in contrast to pWT1, pPH3 contained DI-like termini, i.e., complimentary termini surrounding a partial L gene (FIG. 2). As with pWT1, the panhandle-type genomic analog sequences were also placed in the transcription plasmid under T7 promoter control and followed by the HDV ribozyme and T7 terminator. T7 RNA polymerase transcription of pPH3 would produce 1261-nt long negative-sense RNA consisting of the 155-nt trailer at the 5' end, 75-nt of the trailer's complement at the 3' end and 1031-nt L gene end in the middle. After autolytic cleavage, the 3' end of the panhandle-type RNA analog should be exactly complementary to the authentic 5' end of the genome.

To examine the ability of these two constructs to generate transcripts of the appropriate length in 293 cells, pWT1 and pPH3 were transfected in to vTF7-3 infected cells, respectively, and RNAs were labeled with [$^3$H]uridine for 8 hours at 16 hours posttransfection. The total cytoplasmic RNA species synthesized during this period was analyzed by electrophoresis on agarose-urea gel. A major species of labeled RNA of 1.6 Kb from the pWT1 transfected sample and 1.2 Kb from the pPH3 transfected sample was observed, but not in vTF7-3 infected only and the uninfected cells. The minor bands migrating slightly slower than the major negative-sense RNA transcripts were RNA that had not undergone the autolytic cleavage by the time of analysis. The identity of these cleaved and uncleaved transcripts was confirmed later by comparison with the cleaved and uncleaved transcripts from the same plasmids generated by in vitro transcription. More than 90% of the transcripts synthesized during the labeling period was cleaved by the ribozyme, releasing a 200 base RNA that contained the ribozyme and terminator sequences and that migrated near the bottom of the gel.

Encapsidation and Replication of Genomic RNA Analogs

To determine whether the RNAs transcribed in cells by T7 polymerase could be encapsidated with the nucleocapsid protein and replicated, vTF7-3-infected cells were transfected with pWT1 or pPH3 and combinations of plasmids encoding the N, P and L proteins. At 16 hours posttransfection, the cells were exposed to [$^3$H]uridine for 6 hours. Encapsidated and replicated RNAs were selected by immunoprecipitation and analyzed on an agarose-urea gel. Immunoprecipitation of [$^3$H] labeled RNA by anti RS virus polyclonal serum demonstrated that encapsidation of WT and PH type RNA analogs occurred when pRSV-N, pRSV-P and pRSV-L were cotransfected. However, in the absence of pRSV-L, encapsidated RNA was barely detected. These results suggested that during the labeling period, RNA synthesis by the T7 polymerase was not the major event; instead, the T7 transcripts synthesized prior to labeling were encapsidated and functioned as templates for RNA replication by RS virus polymerase. To test whether this was so, the effect of actinomycin D on synthesis and encapsidation of RNA was analyzed. Actinomycin D inhibits DNA dependent RNA synthesis, but not RNA dependent RNA synthesis.

In the presence of actinomycin D, incorporation of [$^3$H] uridine into RS virus genomic analog was completely blocked when only pRSV-N and pRSV-P were present in the cotransfection. However, when pRSV-L was included in the cotransfection, synthesis of the genomic analog was resistant to the drug and readily detected. The results demonstrated that the RNAs were indeed the products of replication by the RS virus polymerase. The majority of encapsidated RNAs represent the replicated RNAs However, the amount of RNA replicated from the wild-type genomic analog is much less than that from the panhandle one, although a similar molar ratio of plasmids was used in the transfection. Due to its higher RNA replication efficiency, the panhandle type analog pPH3 was used as a model to determine the trans-acting protein requirements for RNA replication and to detect the strand-specific RNA synthesis.

The N, P and L Proteins are the Minimal Trans-acting Protein Requirements for RNA Replication To determine the minimal trans-acting protein requirements for RS virus genomic RNA replication, and to optimize the conditions of RNA replication, pPH3 transfected-cells were cotransfected with various combinations of plasmids encoding the N, P and L proteins. At 16 hours posttransfection, the cells were labeled with [$^3$H]uridine in the presence of actinomycin D for 6 hours. The RNAs extracted from cell lysates were analyzed by electrophoresis on an agarose-urea gel. The results clearly showed that any combination of two of these three plasmids in the cotransfection did not support RNA replication. Only when all three plasmids were present in the cotransfection did replication of the panhandle-type RNA analog occur. This clearly defined that the N, P and L proteins were the minimal trans-acting protein requirements for RNA replication of the RS virus genomic analog. As the amount of pRSV-L was increased from 0.25 ug–1 ug in the cotransfection, the yield of replicated RNA products also increased. However, when 2 ug of pRSV-L was cotransfected, the efficiency of replication no longer increased.

It appears that the maximum RNA replication observed occurs when the molar ratio of transfected N, P and L genes is 12:5:1. To test the specificity of the requirement for the viral RNA dependent RNA polymerase for RS virus RNA replication, a VSV L gene plasmid that had been shown to support VSV RNA replication in a similar system (Pattnaik, A. K. et. al., (1992) Infectious defective interfering particles of VSV from transcripts of a cDNA clone. *Cell* 69:1011–1020); Wertz, G. et al., (1994) *Proc. Natl. Acad. Sci. USA*, 91 8587–8591) and a truncated from of RS virus L gene plasmid that expressed a 170 kDa polypeptide were used to replace pRSV-L in the cotransfection. Neither the heterologous polymerase nor the truncated RS virus polymerase supported RNA replication. These data demonstrate that the RNA replication of the genomic analog indeed requires RS virus specific and functional polymerase.

RNase Protection Assay Demonstrates the Synthesis of Positive-strand RNA

During RNA replication of negative-stranded RNA viruses, the encapsidated negative sense genome must first replicate a positive sense RNA antigenome. Consequently, the nascent positive-sense RNA antigenome would be encapsidated to serve as a template for the synthesis of negative-strand RNA progeny. Therefore, the synthesis of the intermediate positive-sense RNA is critical evidence for establishing that RNA replication has occurred. To test RS virus positive-strand RNA synthesis, an RNase protection assay was carried out with a strand-specific probe. Encapsidated RNA was selected by immunoprecipitation from cells cotransfected with pPH3 and combinations of the N, P and L gene plasmids. A 391-nt long, [$^{35}$S]-labeled RNA probe was used, of which 360 nucleotides were transcribed from the L gene sequences and complementary to the positive-sense RNA, and the other 31 nucleotides corresponded to the polylinker region of the vector. Hybridization of the probe with the positive-strand RNA should produce a double strand RNA hybrid which, after nuclease digestion to remove the overhanging nucleotides, would be 360 base pairs long.

Indeed, electrophoretic analysis of the protected RNA products demonstrated that the positive-strand RNA was synthesized when all three viral N, P and L gene plasmids were cotransfected, but not in the absence of the L gene plasmid in the cotransfection. This protected RNA product migrated at the predicted size (360 nt). The undigested probe (391 nt) hybridized with yeast RNA and was completely degraded following treatment with RNase, thus indicating that the nuclease digestion was complete. These data demonstrated that positive-strand RNA was replicated from the initial negative sense RNA transcribed in cells, and confirmed that RNA replication occurred only when all three viral proteins, N, P and L were provided by cotransfection.

Equivalents

Those skilled in the art will recognize, or be able to ascertain using no more than routine experimentation, many equivalents of the specific embodiments of the invention described herein. Such equivalents are intended to be encompassed by the following claims.

We claim:

1. A pure, recombinant, virus particle, which, upon entering a host cell, replicates and buds progeny virions, comprising: 1) a functional non-segmented respiratory syncytial virus RNA dependent RNA polymerase (L); 2) a non-segmented respiratory syncytial virus phosphoprotein (P); 3) a non-segmented respiratory syncytial virus nucleocapsid (N); 4) necessary non-segmented respiratory syncytial virus structural proteins; 5) a 3' non-coding RNA sequence; 6) a 3' to 5' RNA coding region; and 7) a 5' non-coding RNA sequence, wherein components 1 thru 7 are from the same species of non-segmented respiratory syncytial virus.

2. A virus particle of claim 1, wherein said respiratory syncytial virus is a human respiratory syncytial virus.

3. A virus particle of claim 1, wherein said respiratory syncytial virus is a bovine respiratory syncytial virus.

4. A pure, recombinant, replicating and non-spreading non-segmented RNA virus particle, comprising: 1) a functional non-segmented respiratory syncytial virus RNA dependent RNA polymerase (L); 2) a non-segmented respiratory syncytial virus phosphoprotein (P); 3) a non-segmented respiratory syncytial virus nucleocapsid (N); 4) necessary respiratory syncytial virus infection proteins; 5) a 3' non-coding RNA sequence; 6) a 3' to 5' RNA coding region, which encodes said non-segmented virus L, P, N, but no non-segmented virus structural proteins required for assembly of budded infectious particles; and 7) a 5' non-coding RNA sequence, wherein components 1 thru 7 are from the same species of non-segmented respiratory syncytial virus.

5. A virus particle of claim 4, wherein said respiratory syncytial virus is a human respiratory syncytial virus.

6. A virus particle of claim 4, wherein said respiratory syncytial virus is a bovine respiratory syncytial virus.

7. A pure, recombinant, virus particle, comprising: 1) a functional non-segmented respiratory syncytial virus RNA dependent RNA polymerase (L); 2) a non-segmented respiratory syncytial virus phosphoprotein (P); 3) a non-segmented respiratory syncytial virus nucleocapsid (N); 4) non-segmented respiratory syncytial virus structural proteins; 5) a 3' non-coding RNA sequence; 6) a 3' to 5' RNA coding region; and 7) a 5' non-coding RNA sequence, wherein components 1 thru 7 are from the same species of non-segmented respiratory syncytial virus.

8. virus particle of claim 7, wherein said respiratory syncytial virus is a human respiratory syncytial virus.

9. A virus particle of claim 7, wherein said respiratory syncytial virus is a bovine respiratory syncytial virus.

10. A method for recovering wildtype or recombinant negative stranded, non-segmented respiratory syncytial virus genomes, comprising; transfecting a cultured host cell with one or more nucleic acid molecules, coding for: 1) a functional non-segmented respiratory syncytial virus RNA dependent RNA polymerase (L); 2) a non-segmented respiratory syncytial virus phosphoprotein (P); 3) a non-segmented respiratory syncytial virus nucleocapsid (N); 4) a 3' non-coding RNA sequence; 5) a 3' to 5' RNA coding region; and 6) a 5' non-coding RNA sequence, wherein components 1 thru 6 are from the same species of non-segmented respiratory syncytial virus, and wherein components 1 thru 6 are expressed in said transfected host cell and are operably linked to form said virus genome.

11. A method of claim 10 in which the functional L, N, and P proteins are expressed from plasmids.

12. A cultured host cell made by the process of claim 10.

* * * * *